(12) United States Patent
Chernyak et al.

(10) Patent No.: US 7,098,328 B2
(45) Date of Patent: Aug. 29, 2006

(54) METHOD FOR THE PREPARATION OF 6α-FLUORO CORTICOSTEROIDS

(75) Inventors: Shimon Chernyak, Yokneam Yllit (IL); Martin Zarbov, Kiriat Haim (IL); Daniella Gutman, Rishon LeZion (IL)

(73) Assignee: Taro Pharmaceutical Industries Limited, Haifa (IL)

( * ) Notice: Subject to any disclaimer, the term of this patent is extended or adjusted under 35 U.S.C. 154(b) by 151 days.

(21) Appl. No.: 10/305,138

(22) Filed: Nov. 27, 2002

(65) Prior Publication Data
US 2003/0162959 A1 Aug. 28, 2003

Related U.S. Application Data

(60) Provisional application No. 60/333,752, filed on Nov. 29, 2001.

(51) Int. Cl.
C07J 71/00 (2006.01)
C07J 7/00 (2006.01)
C07J 5/00 (2006.01)

(52) U.S. Cl. .................. 540/88; 552/569; 552/570; 552/573; 552/574

(58) Field of Classification Search ............. 540/88; 552/569, 570, 573, 574
See application file for complete search history.

(56) References Cited

U.S. PATENT DOCUMENTS

| | | | | |
|---|---|---|---|---|
| 4,036,831 | A | 7/1977 | Loken et al. | 260/239.55 R |
| 4,255,331 | A | 3/1981 | McDonald | 260/239.55 R |
| 4,576,936 | A | 3/1986 | McDonald | 514/180 |
| 4,619,921 | A | 10/1986 | Kalvoda et al. | 514/180 |
| 5,086,178 | A | 2/1992 | Banks | |
| 5,478,957 | A | 12/1995 | Godard et al. | 552/610 |
| 5,556,965 | A | 9/1996 | Godard et al. | 540/87 |
| 6,528,666 | B1 | 3/2003 | Villax et al. | 552/295 |
| 6,664,391 | B1 | 12/2003 | Banks et al. | 544/180 |
| 6,794,503 | B1 | 9/2004 | La Loggia et al. | 540/87 |
| 2002/0062021 | A1* | 5/2002 | La Loggia et al. | 540/76 |

FOREIGN PATENT DOCUMENTS

| | | |
|---|---|---|
| CH | 631 185 | 7/1982 |
| EP | 0 610 138 A1 | 8/1994 |
| EP | 1 207 166 A2 | 5/2002 |
| GB | 1 563 638 | 3/1980 |
| JP | 60-6700 * | 1/1985 |
| WO | WO 02/100878 A1 | 12/2002 |
| WO | WO 03/047329 A2 | 6/2003 |
| WO | WO 04/052911 A1 | 6/2004 |

OTHER PUBLICATIONS

J. Kalvoda et al., "Concept and Development of a Potent Topical Corticosteroid", Chirnia 46, No. 7/8 (1992) 338-344.
R.E. Banks, "SelectfluorTM Reagent F-TEPA-BF4 in Action: Tamed Fluorine at Your Service", UMIST, Manchester, 1997.
M. Hudlicky and A.E. Pavlath (ed.), "Chemistry of Organic Fluorine Compounds II", ACS Monograph 187, Washington, DC 1995, pp. 163-164.
R.E. Banks et al., "1-Alkyl-4-fluoro-1,4-diazoniabicyclo[2.2.2]octane Salts: a Novel Family of Electrophilic Fluorinating Agents", J. Chem. Soc., Chem. Commun. (1992) 595-596.
R.E. Banks et al., "Efficient Electrophilic Fluorination of b-Dicarbonyl Compounds with the Selectfluor Reagent F-TEDA-BF4 {1-Chloromethyl-4-fluoro-1,4-diazoniabicyclo[2.2.2]octane bis(tetrafluoroborate)}", J. Chem. Soc., Chem. Commun. (1994) 343-344.

(Continued)

Primary Examiner—Brenda Coleman
(74) Attorney, Agent, or Firm—Siu K. Lo, Esq.

(57) ABSTRACT

A method for producing a 6α-fluorinated corticosteroid or derivative thereof by reacting a 17-hydroxy-21-ester epoxide of Formula II

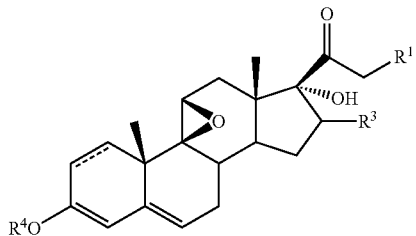

II with a stereoselective fluorinating agent to stereoselectively form a 21-ester-17-hydroxy 6α-fluorinated compound of Formula VII

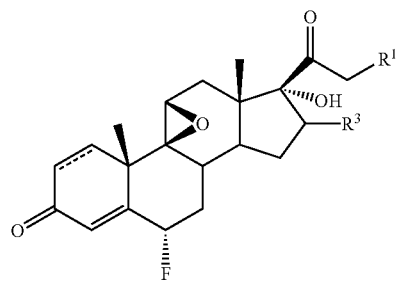

VII $R^1$ can be OC(O)—$R_d$; $R^4$ can be C(O)—$R_d$; $R^3$ can be H or $R_d$. Each $R_d$ may be the same or different and is independently selected from $(C_{1-4})$alkyl, aryl and heteroaryl. The dashed line can be a single or a double bond. $R^4$ may be, for example, acetyl; $R^3$ may be, for example, alpha or beta methyl; $R^1$ may be, for example, acetate or propionate. The stereoselective fluorinating agent used in the reaction may be, for example, a fluoropyridinium or fluoroquinuclidium compound, for example, Selectfluor®.

8 Claims, No Drawings

OTHER PUBLICATIONS

G.S. Lal, "Fluorination at C2', C3', and C5' of nucleosides with 1-chloromethyl-4-fluoro-1,4-diazabicyclo[2.2.2]octane bis(tetrafluoroborate) SelectfluorTM reagent", Syn. Commun. 25, No. 5 (1995) 725-737.

G.S. Lal, "Site-Selective Fluorination of Organic Compounds Using 1-Alkyl-4-fluoro-1,4-diazabicyclo[2.2.2]octane Salts (Selectfluor Reagents)", J. Org. Chem. 58 (1993) 2791-2796.

M.A. McClinton and V. Sik, "5-Fluorocyclopentadiene: Synthesis and Utility", J. Chem. Soc., Perkin Trans. I (1992) 1891-1895.

M. Brunavs et al., "Direct fluorination of the anthraquinone nucleus: scope and application to the synthesis of novel rhein analogues", J. Fluorine Chem. 68 (1994) 201-203.

D.P. Matthews et al., "A new method for the electrophilic fluorination of vinyl stannanes"., Tetrahedron Letters 34, No. 19 (1993) 3057-3060.

H.F. Hodson et al., "Electrophilic Fluorination in the Synthesis of New Fluoroindoles", Tetrahedron 50, No. 6 (1994) 1899-1906.

S. Stavber et al., "A Mild, Selective Method for Preparation of Vicinal Fluoro Ethers Using 'F-Teda-BF4 '", Tetrahedron Letters 35, No. 7 (1994) 1105-1108.

M. Zupan et al., "Solvent effects in the fluorination of aromatic molecules with 'F-TEDA-BF4 '", J. Fluorination Chem. 70 (1995) 7-8.

S. Stavber and M. Zupan, "A New, Selective Method for Conversion of Alcohols to Vicinal Fluorohydrins", J. Chem. Soc., Chem. Commun. (1994) 149-150.

S. Budavari, "The Merck Index", Merck & Co., Whitehouse Station, NJ, 1996, pp. 530-531.

V.M. Baghdanov, "Fluorinated Compounds: Synthesis by Fluorination", TCI America, Fall (1995) at http://www.tciamerica.com/news/newslib/95fat_a.htm.

"Fluorinating Agents", Tosoh (2002) at http://www.f-techinc.co.jp/pages/efluorinationin.html.

"Selectfluor® Fluorinating Reagent", Air Products (2001) at http://www.airproducts.com/fluorination/selectfluor.asp.

D. Cahard et al., "Enantioselective Electrophilic Fluorination: Two Approaches Using Cinchona Alkaloids", 4th Int'l Electronic Conf. on Syn. Organic Chem (ECSOC-4), Sep. (2000) at http://www.unibas.ch/mdpi/ecsoc-4/a0081/a0081.htm.

* cited by examiner

METHOD FOR THE PREPARATION OF 6α-FLUORO CORTICOSTEROIDS

This application claims priority under 35 U.S.C. § 119(e) of Provisional Application Ser. No. 60/333,752, filed Nov. 29, 2001, the disclosure of which is incorporated by reference in its entirety herein.

BACKGROUND OF THE INVENTION

1. Field of the Invention

The present invention relates to the manufacture of 6α-fluorinated corticosteroids. In particular, the invention relates to the manufacture of 6α,9α-difluoro-11β,17α,21-trihydroxy-16α(or β)-methyl-prednisolones and their 17- and/or 21-substituted derivatives.

2. Related Art

Certain halogenated corticosteroids, particularly 6α,9α-difluoro-11β,17α21-trihydroxy-16α(or β)-methyl-prednisolones and their 17- and/or 21-substituted derivatives, represented generally by compound I ($R^3$=Me), are known anti-inflammatory agents having pronounced activity.

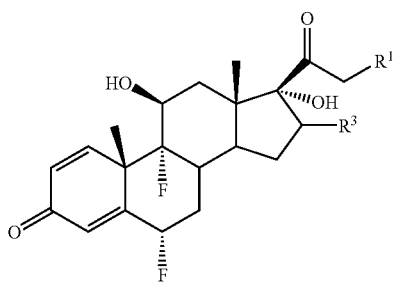

I

Examples of compounds in this class include diflorasone ($R^1$=OH, $R^3$=β-methyl), flumethasone ($R^1$=OH, $R^3$=α-methyl), and halobetasol propionate. These agents have a 6-fluoro substituent exclusively in the alpha-(equatorial) configuration. Derivatives of these compounds, e.g., diflorasone diacetate, halobetasol propionate, flumethasone acetate etc., have also been shown to have enhanced anti-inflammatory activity.

Traditional methods for inserting fluorine in the 6-position of the steroid molecule consist of converting the corresponding 3-ketosteroids into appropriate 3-enolates and reacting these unstable intermediates with a source of electrophilic fluorine. Common sources of electrophilic fluorine that have been used are frequently toxic and gaseous, for example perfluoryl perchlorate. These known procedures generally lead to mixtures of both the 6-α- and 6-β-diastereomers which must then be separated by, for example, crystallization or column chromatography. For pregn-4-enes, the relative amount of alpha-epimer may be increased by bubbling anhydrous hydrogen chloride through a mixture of isomers in an inert organic solvent (See, for example, U.S. Pat. No. 4,036,831).

U.S. Pat. No. 4,255,331 discloses a method of preparing diflorasone derivatives which includes, as a key step, 6-fluorination of 9β,11β-epoxy-16-β-methylpregna-1,4-diene-3,20-dione 17,21-diesters. This conversion was performed in two steps by the formation of unstable 3-enolacetate and reaction of this derivative with fluoroperchlorate.

A second method (Kavolda et al. *Chimia* 46, 1992, pp. 338–344; Swiss. Pat. 631185; GB1563638) includes hydrogenation of the 1,2-double bond of pregna-1,4-diene-3,20-dione, preparation of the 3-ethyl enolate, 6-fluorination of the enolate by fluoroperchlorate and oxidation of the 6-fluoropreg-4-ene with DDQ to restore the pregna-1,4-diene configuration. Although this reaction proceeds with some stereoselectivity, it also utilizes the explosive and toxic gaseous fluoroperchlorate as the source of electrophilic fluoride. This reagent "has become a reagent with limited appeal. Its loss of popularity stems from difficult handling, threatening explosions, unwanted chlorinated by-products, and unavailability" (M. Hudlicky, A. E. Pavlath (ed.), "Chemistry of Organic Fluorine Compounds II", ACS, Washington, D.C. 1995, pp. 163, 164).

There thus remains a need for safe and effective methods of preparing fluorinated steroids that are useful as anti-inflammatory agents. There is also a continuing need for methods of forming these compounds in a stereoselective manner.

SUMMARY OF THE INVENTION

In summary, the present invention is the reaction of a stereoselective fluorinating agent with epoxidized corticosteroids esterified at the 21-position without esterification of the 17-position, to stereoselectively obtain a 6-alpha-fluoro derivative. These useful intermediates may then be transformed into other derivatives and analogs such as 6α-fluoro and 6α,9α-difluoro corticosteroids. The invention is thus a safe, effective and stereoselective route to a broad range of compounds having potential use as potent anti-inflammatory agents.

This invention succeeds where previous efforts have failed by providing a safe, effective and stereoselective synthesis of 6-α-fluorinated corticosteroids, such as, for example, 6α,9α-difluoro-11β,17α,21-trihydroxy-16α(or β)-methyl-prednisolones and their 17- and/or 21-substituted derivatives. Prior methods have relied on explosive, toxic and gaseous reagents and/or required separation of epimeric or diastereomeric mixtures, particularly the 6-beta-fluoro epimer.

This invention differs from the prior art in modifications which were not previously known or suggested by developing novel methods of 6-α-fluorocorticosteroid synthesis.

This invention satisfies a long felt need for a safe, effective and stereoselective processes for preparing known corticosteroid anti-inflammatory agents of enhanced potency. The invention may be further used to develop syntheses for other new steroid derivatives.

The invention is a method for producing a 6α-fluorinated corticosteroid or derivative thereof by reacting an epoxide of Formula II

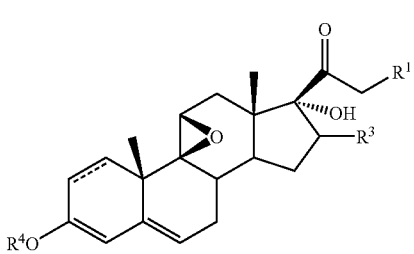

II with a stereoselective fluorinating agent to stereoselectively form a compound of Formula VII

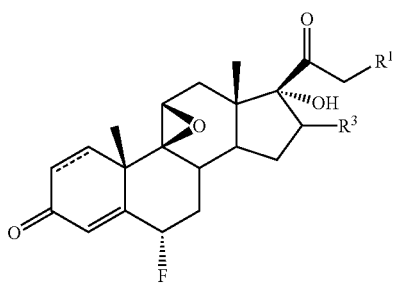

VII where $R^1$ is OC(O)—$R_d$, $R^4$ is C(O)—$R_d$, $R^3$ is H or $R_d$ and the dashed line is a single or double bond; and each $R_d$ may be the same or different and is independently selected from $(C_{1-4})$alkyl, aryl, and heteroaryl. $R^4$ may be, for example, acetyl; $R^3$ may be, for example, alpha, or beta methyl; $R^1$ may be, for example, acetate or propionate. The stereoselective fluorinating agent used in the reaction may be, for example, a fluoropyridinium or fluoroquinuclidium compound, for example, Selectfluor®, 1-fluoropyridinium triflate, 1-fluoropyridinium tetrafluoroborate, or 1-fluoropyridinium pyridine heptafluorodiborate.

Further derivatives may be prepared. For example, a 17-ester may be formed by reaction with a mild esterification reagent, for example a trialkyl orthoester such as trimethyl orthoformate, triethyl orthopropionate or trimethyl orthoacetate. A 9α-fluoro group and 11-hydroxy group may be formed by ring opening of the epoxide using HF. Also, the 21-ester may be hydrolyzed and re-esterified using an acid anhydride.

In an exemplary embodiment of the invention, diflorasone and derivatives thereof can be prepared by reacting an epoxide of Formula XX

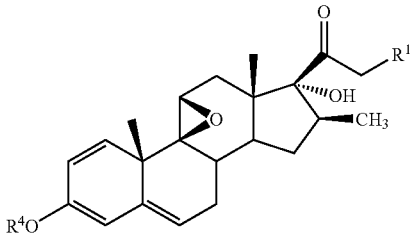

XX with a stereoselective fluorinating agent to stereoselectively form a compound of Formula XXI

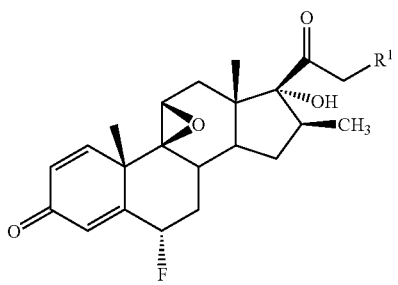

XXI having $R^1$=OC(O)—$R_d$ and $R^4$=C(O)—$R_d$; where each $R_d$ may be the same of different and is independently selected from $(C_{1-4})$alkyl, aryl and heteroaryl; and converting the compound of formula XXI to diflorasone or a derivative thereof. For example, $R^1$ may be acetate, $R^4$ may be acetyl and the stereoselective fluorinating agent may be Selectfluor®. The compound of Formula XXI may be converted to diflorasone or a derivative thereof by 9α-fluorination and epoxide ring opening with HF, and ester hydrolysis using a weak base.

In another exemplary embodiment, the invention may be used as a method of preparing flumethasone and derivatives thereof by reacting an epoxide of Formula XXII

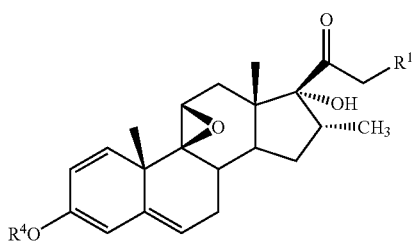

XXII with a stereoselective fluorinating agent to stereoselectively form a compound of Formula XXIII

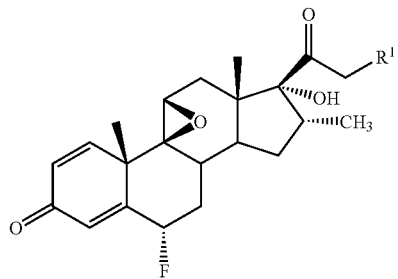

XXIII having $R^1$=OC(O)—$R_d$ and $R^4$=C(O)—$R_d$; where each $R_d$ may be the same or different and is independently selected from $(C_{1-4})$alkyl, aryl, and heteroaryl; and converting the compound of formula XXIII to flumethasone or a derivative thereof. For example, $R^1$ may be acetate, $R^4$ may be acetyl, and the stereoselective fluorinating agent may be Selectfluor®. The compound of Formula XXIII may be converted to flumethasone or a derivative thereof by 9α-fluorination and epoxide ring opening with HF, and ester hydrolysis using a weak base.

In yet another embodiment, halobetasol propionate may be prepared from a compound of Formula XXI. $R^1$ may be, for example, acetate, $R^4$ may be, for example, acetyl, and the compound of formula XXI may be converted into halobetasol propionate by, for example, (1) 9α-fluorination and epoxide ring opening by reaction with HF; (2) ester hydrolysis using a weak base; (3) formation of a 17-propionate ester by reaction with trimethyl orthoacetate; (4) formation of a 21-mesylate by reaction with mesyl chloride; and (5) reacting the 21-mesylate with a chloride containing salt.

Another aspect of the invention is a method for converting obtained 6α-fluoro derivatives of formula I obtained from the reaction into diflorasone or flumethasone.

The invention also provides a method for the synthesis of diflorasone or flumethasone and corresponding derivatives substituted in 21- and/or 17-position.

Further objectives and advantages, as well as the structure and function of preferred embodiments will become apparent from a consideration of the description, and examples.

DETAILED DESCRIPTION

Embodiments of the invention are discussed in detail below. In describing embodiments, specific terminology is employed for the sake of clarity. However, the invention is not intended to be limited to the specific terminology so selected.

A person skilled in the relevant art will recognize that other compounds and derivatives can be prepared without parting from the spirit and scope of the invention. The invention is the highly stereoselective 6α-fluorination of enolized 21-esters of 17-hydroxy-9β,11β-epoxy-16-β-methyl-pregna-3,5-diene-3,20-dione of formula II by stereoselective fluorination agents. Fluorination of these substrates results in highly stereospecific reactions not previously observed in the art. The 6α-fluorinated compounds formed are useful as intermediates in the improved synthesis of 6α-fluoro corticosteroids including, for example, diflorasone and related compounds and their analogs and derivatives.

Preparation of 6α-Fluoro Intermediates

Surprisingly, fluorination of a 17-hydroxy, 21-ester steroidal compound using Selectfluor® and related fluorinating agents differs greatly from known fluorination reactions with similar substrates. Use of the substrates according to the invention results in a highly stereospecific yield in which 6α-fluorination was favored. A 21-ester enol lacking the 17-ester group and having formula II ($R^1$=OCO—$C_1$–$C_4$-alkyl, aryl, heteroaryl; $R^3$=α or β-Me; $R^4$=Ac), for example, 17-hydroxy-9β,11β-epoxy-16(α or β)-methylpregna-3,5-diene-20-dione 21-acetate and 21-propionate, led primarily to the 6α-epimers of general formula

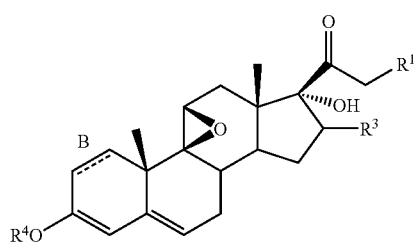

II

VII ($R^1$=OCO—$C_1$–$C_4$-alkyl, aryl, heteroaryl; $R^3$=α or β-Me). Ratios as high as 95:5 (α:β) were typically obtained.

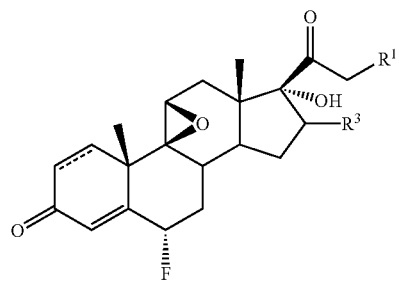

Selectfluor® is a safe fluorination reagent which replaces fluorine perchlorate. Fluorine perchlorate, previously used to prepare 6α-fluoro derivatives of corticosteroids, is difficult to handle. Other similar fluorinating reagents are known and are disclosed in, for example, U.S. Pat. No. 5,086,178, which is incorporated herein by reference in its entirety.

The stereospecific fluorination reactions according to the present invention can be carried out in acetonitrile. Other solvents that can be used include dichloromethane, dimethyl formamide, diethyl ether, and tetrahydrofuran. Alcohols can also be used. However, mixed solvent systems that include alcohol are used for vicinal alkoxy fluorination, and vicinal alkoxy fluorinated compounds can be an expected side product in such solvent systems. Most substrates react readily at room temperature. As used herein, room temperature refers to a temperature in the range of 17–25° C. Less reactive substrates may require higher temperature, including temperatures up to the reflux temperature of the solvent.

The significance of the present invention, which presents a highly stereospecific 6α-fluorination of 17-hydroxy, 21-ester compounds, is highlighted by the fact that previous attempts at 6-fluorination of steroids using the same or similar fluorination reagents have generally resulted in product which was non-stereospecific with respect to the substituted 6-fluorine. When stereospecific fluorination was achieved, the 6β-fluoro configuration predominated. In particular, fluorination of corticosteroid compounds with an ester group at the 17-position does not strongly favor the 6α-fluorinated epimer. For example, fluorination of 9β,11β-epoxy-16β methylpregna-3,5-diene-3,20-diene 17,21-diacetate of general formula VI (where $R^1$=OAc; $R^2$=$R^4$=Ac; $R^3$=Me and B is a single bond) by Selectfluor® led to a mixture of 6α- and 6β-fluoroderivatives, in a ratio of about 4:6 (α:β). The observed reaction is consistent with previous studies in which steroidal compounds were reacted with Selectfluor®. See, for example, R. E. Banks "Selectfluor™ reagent F-TEDA-BF$_4$ in action: tamed fluorine at your service" (describing the reaction of hydrocortisone enol acetate and prednisolone enol acetate to give mixtures of 6α and 6β isomers in ratios of 47:53 and 53:47, respectively), which is incorporated herein by reference in its entirety. Although Lal achieved stereospecificity in fluorinating 3,17α-diacetoxy-3,5-pregnadiene-3,20-dione in the 6-position, β-fluorination was favored; the ratio of stereoisomers was 30:70 (α:β), as presented in G. S. Lal, *J. Org. Chem.* 1993, 58, 2791, which is incorporated herein by reference in its entirety. Studies of fluorination of compounds using Selectfluor® and similar reagents are also presented in the following publications: R. E. Banks et al., *J. Chem. Soc., Chem. Commun.* 1992, 595; G. S. Lal, *Synth. Commun.* 1995, 25 (5), 725; R. E. Banks et al., *J. Chem. Soc., Chem. Commun.* 1994, 343; Zupan, M. et al., *J. Fluorine Chem.,* 1995, 70, 7; D. P. Matthews et al., *Tetrahedron Lett.* 1993, 34 (19), 3057; M. Brunavs et al., *J. Fluorine Chem.* 1994, 201; M. A. McClinton et al., *J. Chem. Soc., Perkin Trans. I,* 1992, 1891; H. F. Hodson et al., *Tetrahedron,* 1994, 50 (6), 1899; S. Stavber & M. Zupan, *J. Chem. Soc., Chem. Commun.* 1994, 149; and S. Stavber et al., *Tetrahedron Lett.* 1994, 35 (7), 1105, each of which is incorporated herein by reference in entirety. In contrast to the present invention, these references generally do not show any particular stereospecificity when using these reagents.

The 17-hydroxy, 21-ester steroids used to form the reactive enol forms, which serve as substrates for the fluorination step, have the general formula V wherein $R^1$=OCOR$_d$ where R$_d$ may be (C$_{1-4}$)alkyl, aryl or heteroaryl. Suitable aryl and heteroaryl compounds include aromatic moieties having six-membered rings, for example phenyl and 2- or 4-pyridyl, as well as-bicyclic aromatic substituents, for example naphthyl, quinolinyl, isoquinylinyl and similar substituents. $R^3$ may be H or substituted as either the α or β epimer with (C$_{1-4}$)alkyl, aryl or heteroaryl, as defined above. Methyl is an exemplary value of $R^3$. The dashed bond at B represents either a single or double bond. These 21-esters are readily prepared from commercially available steroids by known methods ascertainable to persons skilled in the art.

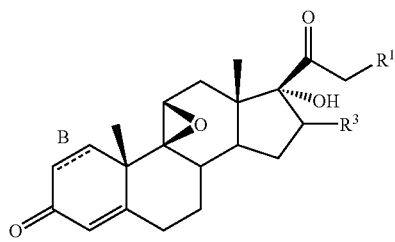

V

Enolization of the 21-esters of formula V is accomplished by known methods to give rise to compounds of formula II, where $R^1$ and $R^3$ are as defined above and $R^4$ is C(O)R$_d$ where R$_d$ may be (C$_{1-4}$)alkyl, aryl or heteroaryl. Suitable aryl and heteroaryl compounds include aromatic moieties having six membered rings, for example phenyl 2- or 4-pyridyl, as well as bicyclic aromatic substituents, for example naphthyl, quinolinyl, isoquinylinyl, and similar substituents. Catalysts can be used in this enolization step; examples of catalysts are sulfuric acid, p-toluenesulfonic acid, methansulfonic acid, or pyridinium tosylate.

In an exemplary method, the 3-acetate ($R^4$=Ac) is formed by the reaction of isopropenyl acetate in mild acid conditions to form enol acetates of formula II ($R^1$=OCO—C$_1$–C$_4$-alkyl, aryl, or heteroaryl; $R^3$=α or β-Me; $R^4$=Ac). The reaction of isopropenyl acetate carried out under more rigorous conditions (higher temperature, excess of strong acid, etc.) gives rise to 17, 21-diester enol acetates of the general formula VI ($R^1$=OCO—C$_1$–C$_4$-alkyl, aryl, heteroaryl; $R^2$=$R^4$=Ac, $R^3$=α or β Me).

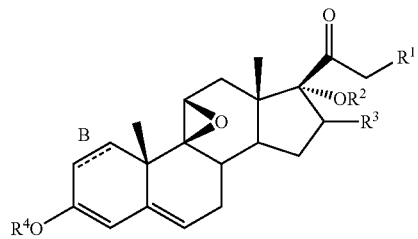

VI

As used herein, "stereoselective fluorinating agents" are compounds that fluorinate enolized 21-esters of 17-hydroxy-9β,11β-epoxy-16-β-methyl-pregna-3,5-diene-3,20-dione and related compounds in the 6-position to stereoselectively produce the α-epimer. Typically, stereoselective fluorinating agents donate an electrophilic fluorine moiety. The α-epimer is considered to be stereoselectively produced if the ratio of 6α-F:6β-F is, for example, about, 60:40 or greater, about 70:30 or greater, about 80:20 or greater, about 95:5 or greater, or if the α-epimer is produced exclusively.

Examples of stereoselective fluorinating agents useful in the present invention include salts of positively charged species having an N—F bond. Several such compounds are known and, for the purposes of the present invention, may be broadly categorized in two classes: fluoropyridiniums and fluoroquinuclidinium compounds, represented by general structures III and IV, respectively. Known fluoropyridinium compounds of formula III useful in practicing the invention include those having

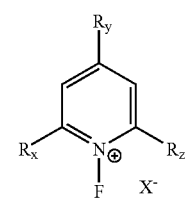

III

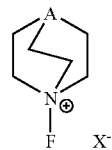

IV $R_x$=$R_y$=$R_z$=H; $R_x$=$R_y$=$R_z$=CH$_3$; and $R_x$=$R_z$=CH$_3$, $R_y$=H. Known fluoroquinuclidinium compounds of formula IV useful in practicing the invention include those having A=CH and A=N$^+$—CH$_2$ClX$^-$. The counterions (X$^-$) for both the fluoropyridiniums and fluoroquinuclidinium compounds are non-nucleophilic anions such as, for example, tetrafluoroborate (BF$_4^-$), phosphorous hexafluoridate (PF$_6^-$) and organic sulfonate esters, e.g. triflate. Fluoropyridinium pyridine heptafluorodiborate is also useful in practicing the invention. It is to be understood that, as used herein, the term fluoropyridiniums and fluoroquinuclidinium implies the presence of a suitable counterion if none is specifically mentioned. A specific example of a fluorinating agent useful for practicing the invention is Selectfluor®, which is available commercially from Air Products, Inc. Selectfluor® is a fluoroquinuclidinium salt having A=N—CH$_2$ClBF$_4^-$ and X=BF$_4^-$ and is also referred to as F-TEDA.

to the 9α-fluorination/ring opening reaction to yield the same difluorocorticosteroids of formula X. Using either of these synthetic routes, diflorasone (R$^3$=β-Me) and flumethasone (R$^3$=α-Me) have been prepared.

Scheme I

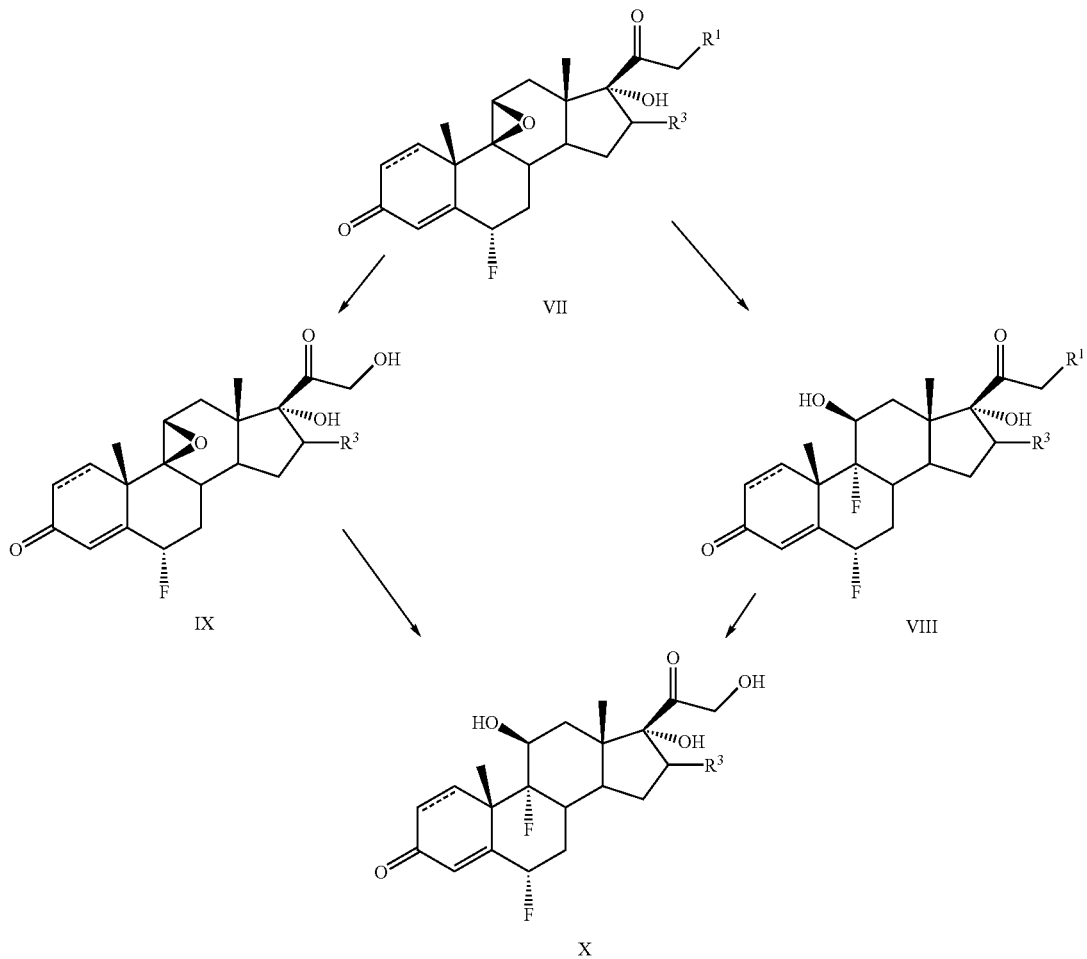

Reactions of 6α-Fluorinated Intermediates

The compounds of general formula VII (R$^1$=OCO—C$_1$–C$_4$-alkyl, aryl, heteroaryl; R$^3$=Me (α or β), are readily converted into known 6α-fluoro corticosteroids and their derivatives. Examples of typical derivatization pathways are outlined in Scheme I. For example, reaction with 70% hydrofluoric acid at low temperatures results in simultaneous 9α fluorination and epoxide ring opening to yield difluorinated corticosteroids of formula VIII. Using this technique, the 21-esters of diflorasone (R$^1$=OCOR; R$^3$=β-Me) and flumethasone (R$^3$=α-Me), including the 21-acetate and 21-propionate esters, have been prepared. Alternatively, the 6α-fluoro corticosteroids of formula VII may be hydrolyzed in mild base, e.g. potassium carbonate, to give rise to the de-esterified epoxides of formula IX. The ester in the difluoride of formula VIII may be hydrolyzed in a like manner to give difluorocorticosteroids of formula X. In an alternate route, the epoxides of formula IX may be subject Corticosteroids of formula X may be used as a starting material for preparing a wide range of 6α-fluorinated corticosteroid derivatives. Without being limited, the most common derivatives that may be prepared using this methodology are compounds formed by further reaction at the 17, 21, and/or 11-hydroxy groups. Such derivatives include, for example, carboxylate, sulfonate, sulfate, sulfite, phosphate, phosphite, phosphonyl and phosphonate esters, carbonates, carbamates, ethers, etc. In addition, derivatives may be prepared by replacing one or more of the hydroxyl groups with other reactive groups, for example, halides (F, Cl, Br, I), nitriles, amines, etc., using chemistry known to persons skilled in the art.

The 6α-fluorinated betamethasone 9,11-oxido 21-acetate (VII, R$^1$=OAc, R$^3$=β-methyl) may be converted into a corresponding 17,21-acetate by action of isopropenyl acetate in the presence of acid or base catalyst. Reaction of this 17,21-diacetate with hydrofluoric acid gives a diflorasone diacetate.

Further analogs of known 9α fluorinated corticosteroids may also be prepared through the intermediate VII. One common approach is to use nucleophiles other than F in the epoxide ring-opening reaction. For example, chloride or bromide may be introduced using hydrochloric or hydrobromic acid, respectively. This would place other substituents at the 9-position, preferably in a stereoselective or stereospecific manner. These compounds can then be derivatized at any of the resultant hydroxy groups, or the nucleophile used in the ring opening reaction may undergo further replacement. Given the increased anti-inflammatory activity observed in the 6α-fluorinated corticosteroids as a class, it is expected that members of this group may be effective, potent anti-inflammatory agents.

Some examples of derivatives and analogs of corticosteroids and their preparation are shown in Schemes II and III. For example, 17-ester derivatives of the general formula XI ($R^2$=CO—$C_1$–$C_4$-alkyl, aryl, heteroaryl) can be formed from the corticosteroid of formula X by reaction with a mild esterification reagent such as a proper trialkyl orthoester. (Scheme II) These products may be further esterified at the 21-position by reaction with an acid anhydride to form 17,21-diesters of formula XII ($R^1$=CO—$C_1$–$C_4$-alkyl, aryl, heteroaryl). Using this methodology, a broad range of diesters derived from the same or different acids may be prepared.

For example, reaction of diflorasone with trimethyl orthoacetate in DMA in presence of p-toluene sulphonic acid (PTSA) leads to diflorasone 17-acetate (Formula XI; $R^2$=Ac, $R^3$=β-Me). This 17-acetate is readily converted into diflorasone 17,21-diacetate through reaction with acetic anhydride in the presence of potassium acetate (Formula XII; $R^2$=$R^1$=Ac, $R^3$=β-Me).

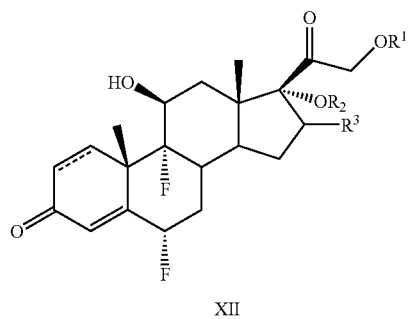

XII

Other 17-esters may be similarly obtained. For example, diflorasone 17-propionate may be obtained by reacting diflorasone with triethyl orthopropionate. Another esterification reagent which may be used is trimethyl orthoformate.

Reaction of the 17-ester and other derivatives is not limited to further esterification, but may be used to produce additional derivatives. For example, as shown in Scheme III, reaction of diflorasone 17-propionate (XIII), prepared as above, with methansulfonyl chloride (MesCl) leads to the mesylate (XIV). The mesylate may then be heated with LiCl in DMA to give halobetasol propionate (XV).

Scheme III

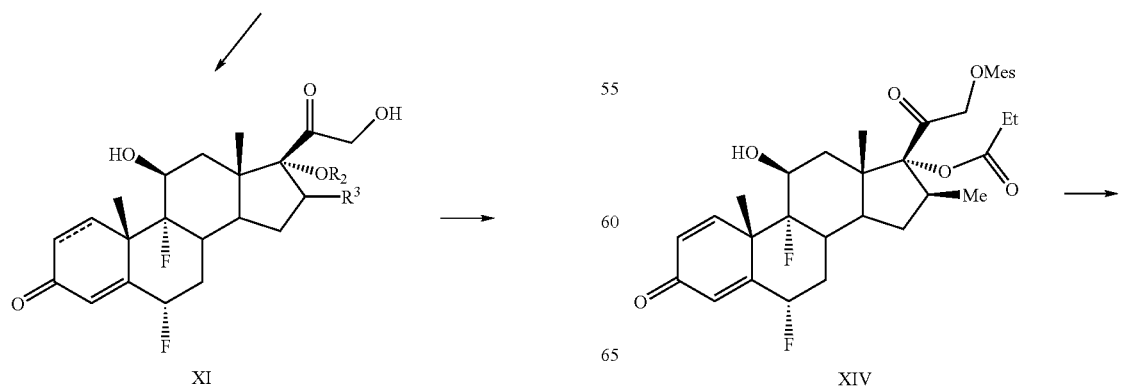

XIII

XIV

Scheme II

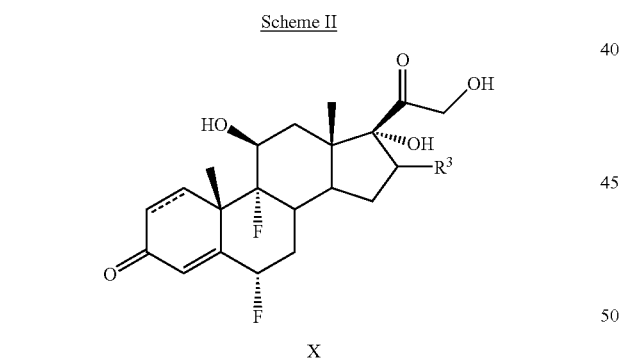

X

XI

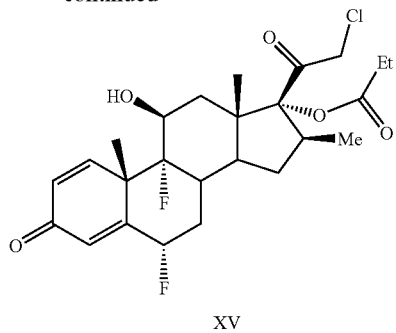

XV

The following non-limiting examples illustrate the novel aspects of this invention. Persons of ordinary skill in the art will recognize that different derivatives may be prepared using known synthetic methods without departing from the invention. Structure were confirmed by spectroscopically or by comparison to a known sample.

It will be appreciated by persons skilled in the art that other acids or acid derivatives can be utilized to prepare a broad range of ester derivatives. These include other sulfonic acid esters, carboxylate esters, phosphate, phosphoric and phosphoric acid esters, etc. These may be esters having $R^1=R^2$ (see for example, Formula XII) or may be mixed acid esters where $R^1$ and $R^2$ are different. Other derivatives may similarly be obtained by reaction with the esters described herein, as well as others. Thus, in addition to its usefulness in preparing known 6α-fluorinated corticosteroids, the present invention is useful for preparing a broad range of new 6α-fluorinated corticosteroid derivatives.

EXAMPLE I

To a solution of 17-hydroxy-9β,11β-epoxy-16-β-methylpregna-1,4-diene-3,20-dione 21-acetate (5.0 g) in isopropylidene acetate (50 ml) was added concentrated sulfuric acid (0.25 ml). The mixture was stirred for 2 hours and the excess sulfuric acid neutralized with triethylamine. The resultant solution was evaporated in a vacuum, the residue dissolved in acetonitrile (50 ml) and F-TEDA (8.0 g) added. The resultant mixture was stirred 1 hour, diluted with water and extracted with ethyl acetate. The organic layer was washed with water and concentrated in vacuum. The residue was triturated with methanol to obtain pure 6-α-fluoro-17-hydroxy-9β,11β-epoxy-16-β-methylpregna-1,4-diene-3,20-dione 21-acetate.

The following steroids of general formula VII were prepared in an analogous manner:
6α-fluoro-17-hydroxy-9β,11β-epoxy-16β-methylpregna-1,4-diene-3,20-dione 21-propionate;
6α-fluoro-17-hydroxy-9β,11β-epoxy-16α-methylpregna-1,4-diene-3,20-dione 21-acetate; and
6α-fluoro-17-hydroxy-9β,11β-epoxy-16-α-methylpregna-1,4-diene-3,20-dione 21-propionate.

EXAMPLE II

Comparative

A solution of 9β,11β-epoxy-16β-methylpregna-1,4-diene-3,20-dione 17,21-diacetate (4 g) in isopropylidene acetate (50 ml) was heated with PTSA (0.4 g) for 2 hours. When the reaction was complete, potassium acetate (4 g) was added and the solvent removed under vacuum. The residue was dissolved in ethanol (40 ml) and reacted with F-TEDA (4 g) for 16 hours. The reaction mixture was poured into water and stirred 2 hours. The white precipitate that formed was filtered, washed with water and dried.

The product thus obtained was found to be a mixture of 60% 6-β- and 40% 6-α-fluoroisomers. A sample practically free from β-isomer was obtained after three crystallizations from methanol.

EXAMPLE III

A cold (−10 to −15° C.) solution of 6α-fluoro-17-hydroxy-9β,11β-epoxy-16β-methylpregna-1,4-diene-3,20-dione 21-acetate (1.62 g) in 70% hydrofluoric acid (25 ml) was stirred for 3.5 hours. The solution was then diluted with 250 ml of water, stirred for 1 hour and the precipitate of diflorasone 21-acetate was filtered.

The following steroids were prepared in an analogous manner:
Diflorasone 21-propionate;
Flumethasone 21-acetate; and
Flumethasone 21-propionate

EXAMPLE IV

A solution prepared from potassium carbonate (0.7 g) and water (7 ml) was added to a suspension of diflorasone 21-acetate (1.4 g) in methanol (15 ml) with stirring. Stirring continued for 3 hrs, and the solution was concentrated in vacuum and the residue diluted with water. The resultant suspension was filtered to obtain diflorasone, which was washed with water and dried.

Flumethasone was prepared in an analogous manner from flumethasone 21-propionate.

EXAMPLE V

A mixture of diflorasone (1 g) and PTSA (0.3 g) was added to N,N-dimethylacetamide (10 ml) and stirred until dissolved. To this solution, trimethyl orthoacetate (1 ml) was added and the solution stirred for 5 hrs. The solution was then diluted with 40 ml of water and stirred additional 3 hrs. Diflorasone 17-acetate formed as a precipitate that was filtered, washed with water and dried.

Diflorasone 17-propionate was prepared by the analogous manner.

EXAMPLE VI

To a solution of diflorasone 17-acetate (2.5 g) in N,N-dimethylacetamide (25 ml), potassium acetate (2.5 g) was added followed by acetic anhydride (3 ml). The mixture was stirred 2 hrs, diluted with water (100 ml) and stirred an additional 2 hrs. A precipitate of diflorasone diacetate formed which was filtered, washed, and dried.

EXAMPLE VII

Triethylamine (4 ml) was added to a solution of diflorasone 17-propionate (3 g) in N,N-dimethylacetamide (30 ml) followed by the addition of methansulfonyl chloride (1.4 ml). The resultant suspension was stirred 1 hour and hydrochloric acid (10 ml, 2N) added. The suspension was stirred an additional 1 hour and a precipitate of diflorasone 17-propionate-21-mesylate formed which was filtered, washed and dried.

EXAMPLE VIII

Diflorasone 17-propionate-21-mesylate (1.5 g) was dissolved in DMA (10 ml) and lithium chloride (0.2 g) added.

The mixture was heated to 100–110° C. and stirred for 3 hrs. The solution was then cooled to 50–55° C., diluted with 10 ml of water and stirred 2 hrs more. A precipitate of halobetasol propionate formed and was filtered, washed with water and dried.

EXAMPLE IX

A solution of potassium carbonate (1.35 g) in water (7 ml) was added to a suspension of 6-α-fluoro-17-hydroxy-9β,11β-epoxy-16-β-methylpregna-1,4-diene-3,20-dione 21-acetate (3 g) in methanol (30 ml). The reaction mixture was stirred 10 hrs, and a precipitate of 6α-fluoro-17,21-dihydroxy-9β,11β-epoxy-16β-methylpregna-1,4-diene-3,20-dione formed. The product was filtered, washed with water and dried.

EXAMPLE X

A solution of 6α-fluoro-17,21-dihydroxy-9β,11β-epoxy-16βmethylpregna-1,4-diene-3,20-dione (2.4 g) in 70% hydrofluoric acid (25 ml) was stirred for 5 hours at −10° to −15° C. The solution was then diluted with 250 ml of water, stirred for 1 more hour and the precipitate of diflorasone was filtered.

EXAMPLE XI

A mixture of 6α-fluoro-17,21-dihydroxy-9β,11β-epoxy-16-β-methylpregna-1,4-diene-3,20-dione (1.0 g) and PTSA (0.78 g) was added to N,N-dimethylacetamide (10 ml) and stirred until dissolved. Trimethyl orthoacetate (0.7 ml) was added and the solution stirred for 3 hrs. The solution was then diluted with water (40 ml) and stirred an additional 3 hrs to form 6α-fluoro-17-hydroxy-9β,11β-epoxy-16β-methylpregna-1,4-diene-3,20-dione 17-acetate as a precipitate which was filtered, washed with water and dried.

EXAMPLE XII

To a solution prepared from 6α-fluoro-21-hydroxy-9β,11β-epoxy-16β-methylpregna-1,4-diene-3,20-dione 17-acetate (2.5 g) in N,N-dimethylacetamide (25 ml), potassium acetate (2.5 g) was added followed by acetic anhydride (3 ml). The reaction mixture was stirred 4 hrs, diluted with water (100 ml) and stirred additional 2 hrs. A precipitate of 6α-fluoro-9β,11β-epoxy-16β-methylpregna-1,4-diene-3,20-dione 17,21-diacetate formed which was filtered, washed and dried.

EXAMPLE XIII

Concentrated sulfuric acid (0.1 ml) was added to a solution of 6α-fluoro-17-hydroxy-9β,11β-epoxy-16-β-methylpregna-1,4-diene-3,20-dione 21-acetate (1.0 g) in isopropylidene (10 ml) acetate (10 ml) and the mixture stirred at 50° C. for 6 hrs. The solution was then neutralized with triethylamine and concentrated in vacuum. The resultant residue was dissolved in water and extracted with ethyl acetate. The organic layer was separated, dried and the solvent removed. The dry residue was triturated with methanol (10 ml) to obtain 6α-fluoro-9β,11β-epoxy-16β-methylpregna-1,4-diene-3,20-dione 17,21-diacetate.

EXAMPLE XIV

A solution of 6α-fluoro-17,21-dihydroxy-9β11β-epoxy-16β-methylpregna-1,4-diene-3,20-dione diacetate (2.0 g ) in 70% hydrofluoric acid (30 ml) previously cooled to −10 to −15° C. was stirred for 3.5 hours. The solution was then diluted with water (250 ml), stirred for 1 hour and the precipitate of diflorasone diacetate (compound XII wherein $R^1$=Ac, $R^2$=Ac, and $R^3$=β-Me) was filtered.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:

1. A method of preparing a 6α-fluorinated corticosteroid, comprising the steps of:

(a) reacting a 21-ester, 17-hydroxy epoxide of Formula XXV

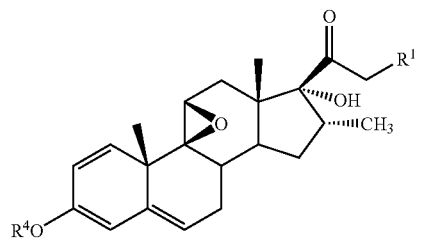

XXII with a stereo selective fluorinating agent to stereo selectively form a 21-ester, 17-hydroxy, 6α-fluorinated compound of Formula XXVI;

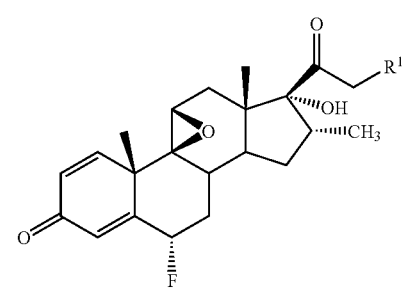

XXIII (b) reacting the 21-ester, 17-hydroxy, 6α-fluorinated compound of Formula XXVI with hydrofluoric acid to form a 21-ester, 11,17-dihydroxy, 6α,9α-difluorinated compound of Formula XXVII; and

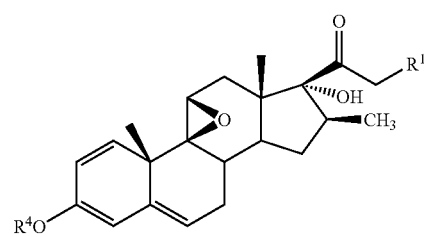

XX (c) reacting the 21-ester, 11,17-dihydroxy, 6α,9α-difluorinated compound of Formula XXVII with a weak base to form a 11,17,21-trihydroxy, 6α,9α-difluorinated compound of Formula XXVIII,

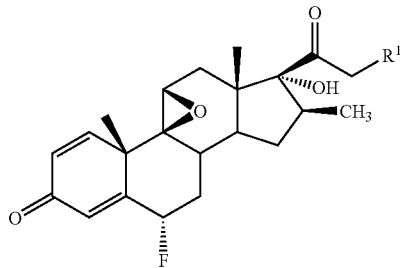

XXI wherein n=1 or 2, and the stereoselective fluorinating agent is selected from the group consisting of 1-chloromethyl-4-fluoro-1,4-diazoniabicyclo[2.2.2]octane bis(tetrafluoroborate), 1-fluoropyridinium triflate, 1-fluoropyridinium tetrafluoroborate, and 1-fluoropyridinium pyridine heptafluorodiborate.

2. The method of claim 1, wherein step (a) is conducted in acetonitrile.

3. The method of claim 1, wherein the compound of Formula XXVIII is diflorasone.

4. The method of claim 1, wherein the compound of Formula XXVIII is flumethasone.

5. The method of claim 3, further comprising the steps of:
(d) reacting the 11,17,21-trihydroxy, 6α,9α-fluorinated compound of Formula XXVIII with trimethyl orthoacetate to form a 17-propionate ester;
(e) reacting the 17-propionate ester with mesyl chloride to form a 21-mesylate; and
(f) reacting the 21-mesylate with a chloride containing salt to form halobetasol propionate.

6. A method of preparing diflorasone, comprising the steps of:
(a) reacting an epoxide of Formula XX

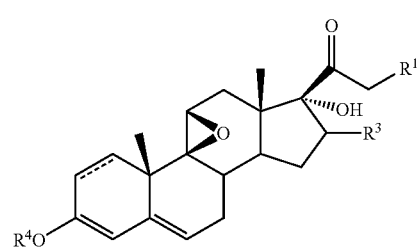

II with a stereoselective fluorinating agent to stereoselectively form a compound of Formula XXI; and

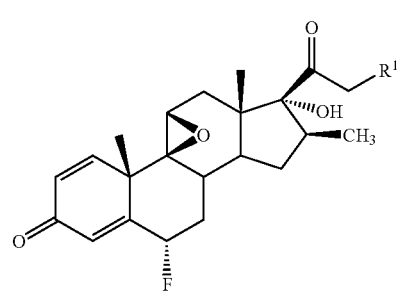

XXI (b) converting the compound of Formula XXI to diflorasone, wherein $R^1$ is OC(O)—$R_d$, $R_4$ is C(O)—$R_d$, and each $R_d$ may be the same or different and is independently selected from the group consisting of ($C_{1-4}$) alkyl, aryl and heteroaryl.

7. The method of claim 6, wherein $R^1$ is acetate, $R^4$ is acetyl, the stereoselective fluorinating agent is 1-chloromethyl-4-fluoro-1,4-diazoniabicyclo[2.2.2]octane bis(tetrafluoroborate) and step (b) further comprises the steps of:
(i) reacting the compound of Formula XXI with HF to form a 9α-fluorinated and epoxide ring-opened ester; and
(ii) hydrolyzing the 9α-fluorinated and epoxide ring-opened ester using a weak base.

8. A method of preparing halobetasol propionate, comprising the steps of:
(a) reacting an epoxide of Formula XX

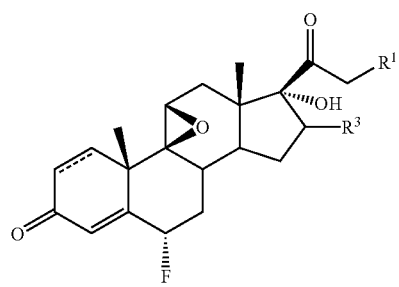

VII with a stereoselective fluorinating agent to stereoselectively form a compound of Formula XXI; and

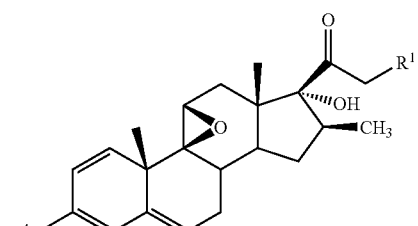

XX (b) converting the compound of Formula XXI to halobetasol propionate, wherein $R^1$ is OC(O)—$R_d$, $R^4$ C(O)—$R_d$, and each $R_d$ may be the same or different and isindependently selected from the group consisting of ($C_{1-4}$)alkyl, aryl and heteroaryl.

* * * * *

UNITED STATES PATENT AND TRADEMARK OFFICE
CERTIFICATE OF CORRECTION

PATENT NO.       : 7,098,328 B2
APPLICATION NO. : 10/305138
DATED            : August 29, 2006
INVENTOR(S)      : Chernyak et al.

It is certified that error appears in the above-identified patent and that said Letters Patent is hereby corrected as shown below:

In claim 1, column 16, lines 21-32, the first structure should be formula XXV

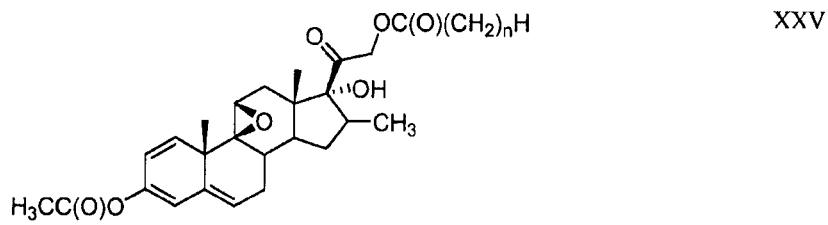

In claim 1, column 16, lines 38-49, the second structure should be formula XXVI

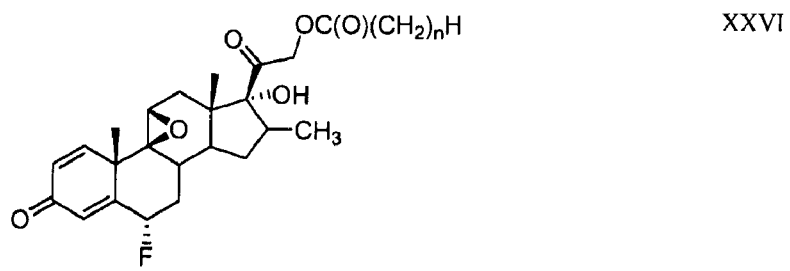

UNITED STATES PATENT AND TRADEMARK OFFICE
CERTIFICATE OF CORRECTION

PATENT NO.      : 7,098,328 B2                              Page 2 of 4
APPLICATION NO. : 10/305138
DATED           : August 29, 2006
INVENTOR(S)     : Chernyak et al.

It is certified that error appears in the above-identified patent and that said Letters Patent is hereby corrected as shown below:

In claim 1, column 16, lines 55-67, the third structure should be formula XXVII

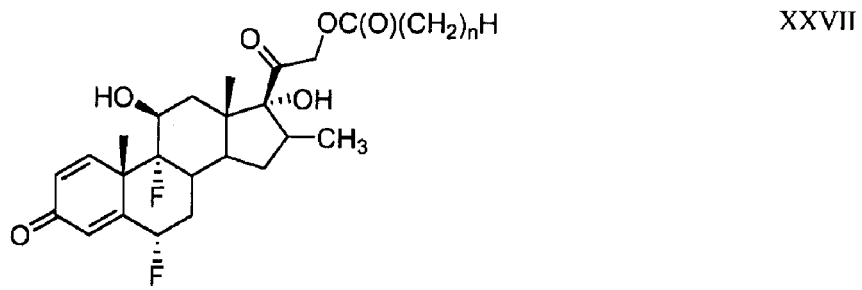

In claim 1, column 17, lines 6-16, the fourth structure should be formula XXVIII

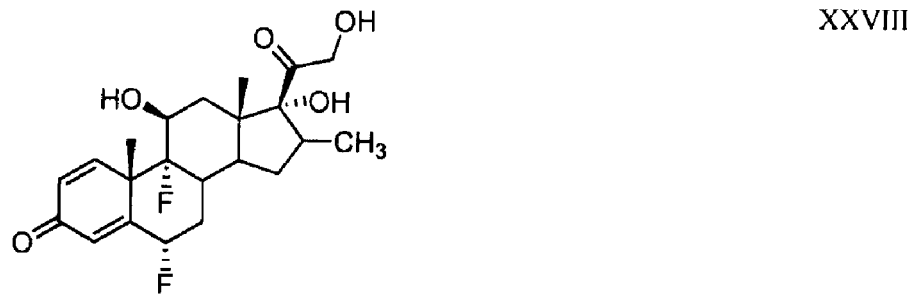

UNITED STATES PATENT AND TRADEMARK OFFICE
CERTIFICATE OF CORRECTION

PATENT NO.       : 7,098,328 B2                                  Page 3 of 4
APPLICATION NO.  : 10/305138
DATED            : August 29, 2006
INVENTOR(S)      : Chernyak et al.

It is certified that error appears in the above-identified patent and that said Letters Patent is hereby corrected as shown below:

In claim 6, column 17, lines 41-51, the first structure should be formula XX

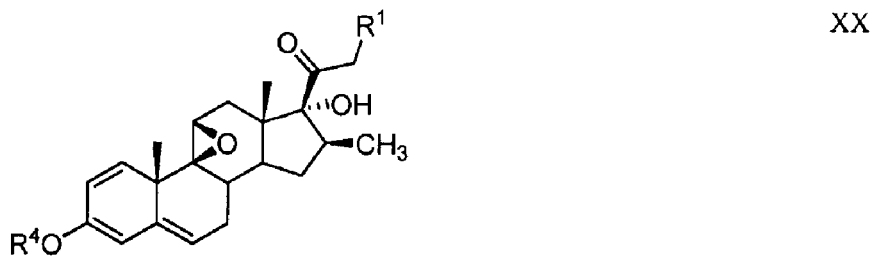

In column 8, column 18, lines 26-37, the first structure should be formula XX

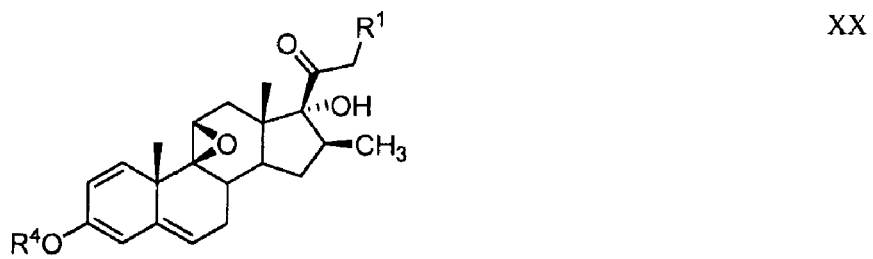

UNITED STATES PATENT AND TRADEMARK OFFICE
CERTIFICATE OF CORRECTION

PATENT NO. : 7,098,328 B2
APPLICATION NO. : 10/305138
DATED : August 29, 2006
INVENTOR(S) : Chernyak et al.

It is certified that error appears in the above-identified patent and that said Letters Patent is hereby corrected as shown below:

In claim 8, column 18, lines 46-57, the second structure should be formula XXI

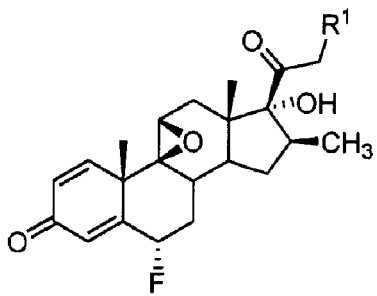

XXI

Signed and Sealed this

Tenth Day of February, 2009

JOHN DOLL
*Acting Director of the United States Patent and Trademark Office*